US010350021B2

(12) United States Patent
Gilgunn et al.

(10) Patent No.: US 10,350,021 B2
(45) Date of Patent: *Jul. 16, 2019

(54) APPARATUS AND METHOD FOR IMPLANTATION OF DEVICES INTO SOFT TISSUE

(71) Applicants: CARNEGIE MELLON UNIVERSITY, a Pennsylvania Non-Profit Corporation, Pittsburgh, PA (US); University of Pittsburgh—Of the Commonwealth System of Higher Education, Pittsburgh, PA (US)

(72) Inventors: Peter J. Gilgunn, Pittsburgh, PA (US); O. Burak Ozdoganlar, Sewickley, PA (US); Takashi Daniel Yoshida Kozai, Pittsburgh, PA (US); Gary Fedder, Turtle Creek, PA (US); Xinyan Cui, Wexford, PA (US); Douglas J. Weber, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 246 days.

This patent is subject to a terminal disclaimer.

(21) Appl. No.: 15/231,699

(22) Filed: Aug. 8, 2016

(65) Prior Publication Data
US 2017/0156815 A1 Jun. 8, 2017

Related U.S. Application Data

(63) Continuation of application No. 13/920,753, filed on Jun. 18, 2013, now Pat. No. 9,408,571.
(Continued)

(51) Int. Cl.
*A61B 5/00* (2006.01)
*A61B 90/10* (2016.01)
(Continued)

(52) U.S. Cl.
CPC ............ *A61B 90/10* (2016.02); *A61B 5/4851* (2013.01); *A61B 5/6838* (2013.01);
(Continued)

(58) Field of Classification Search
CPC ............ A61B 2034/2065; A61B 34/20; A61B 2034/107; A61B 34/10; A61B 5/4851;
(Continued)

(56) References Cited

U.S. PATENT DOCUMENTS 5,361,760 A * 11/1994 Normann ............ A61B 5/04001
600/377
5,601,558 A * 2/1997 Torrie ................ A61B 17/0401
411/495

(Continued)

*Primary Examiner* — Gregory A Anderson
(74) *Attorney, Agent, or Firm* — Michael G. Monyok; David G. Oberdick

(57) ABSTRACT

Apparatus and method for surgeon-assisted rapid surgical implantation of devices into soft tissue. The apparatus comprises several subsystems that enable the referencing of the spatial position and orientation of the device being implanted with respect to the soft tissue into which it is being implanted and then the controlled implantation of the device at a predefined speed with higher positional accuracy and precision and a reduction in soft tissue damage, provided by ultrasonic assisted motion, compared to current state-of-the-art implantation methods and devices. The method includes automated loading of the device being implanted into a clamping mechanism from a cartridge holding a number of implants, referencing of the device position and orientation, referencing of the surface of the tissue into which the device is being implanted, monitoring of the tissue motion, identification of desirable implant location based on the soft tissue profile, allowance of surgeon selection and fine adjustment of the final implant location, high-speed implantation, device release and implant actuator retraction.

8 Claims, 18 Drawing Sheets

Related U.S. Application Data

(60) Provisional application No. 61/690,044, filed on Jun. 18, 2012.

(51) Int. Cl.
  *A61B 34/20* (2016.01)
  *A61B 34/00* (2016.01)
  *A61B 90/00* (2016.01)
  *A61B 34/30* (2016.01)

(52) U.S. Cl.
  CPC ............ *A61B 5/6843* (2013.01); *A61B 34/20* (2016.02); *A61B 34/70* (2016.02); *A61B 34/30* (2016.02); *A61B 2090/064* (2016.02)

(58) Field of Classification Search
  CPC .... A61B 5/6838; A61B 5/6839; A61B 5/6843
  See application file for complete search history.

(56) References Cited

U.S. PATENT DOCUMENTS

| | | | | |
|---|---|---|---|---|
| 5,938,694 A * | 8/1999 | Jaraczewski | ......... | A61B 5/0422 600/373 |
| 6,304,785 B1 * | 10/2001 | McCreery | ............ | A61N 1/0541 128/899 |
| 7,314,474 B1 * | 1/2008 | Greenberg | ........... | A61B 17/064 606/185 |
| 7,340,309 B2 * | 3/2008 | Miazga | ................ | A61N 1/0551 600/372 |
| 7,697,967 B2 * | 4/2010 | Stafford | ............. | A61B 5/14503 600/345 |
| 7,734,342 B2 * | 6/2010 | Gielen | ............... | A61M 5/14276 607/3 |
| 7,831,292 B2 * | 11/2010 | Quaid | ................... | G06F 3/0346 600/424 |
| 8,055,323 B2 * | 11/2011 | Sawyer | ................ | A61N 5/1049 600/407 |
| 2004/0002723 A1 * | 1/2004 | Ball | ....................... | A61F 2/0063 606/180 |
| 2004/0171924 A1 * | 9/2004 | Mire | ..................... | A61B 34/20 600/407 |
| 2007/0156126 A1 * | 7/2007 | Flaherty | ............... | A61B 5/0084 606/32 |
| 2008/0269599 A1 * | 10/2008 | Csavoy | ................. | A61B 90/17 600/426 |
| 2008/0269600 A1 * | 10/2008 | Csavoy | ................. | A61B 90/18 600/426 |
| 2009/0099441 A1 * | 4/2009 | Giszter | ............... | A61N 1/0529 600/377 |
| 2009/0209851 A1 * | 8/2009 | Blau | .................. | A61B 17/1703 600/426 |
| 2009/0275818 A1 * | 11/2009 | Rau | .......................... | A61B 5/06 600/379 |
| 2010/0160771 A1 * | 6/2010 | Gielen | .................. | A61B 34/20 600/424 |
| 2011/0196377 A1 * | 8/2011 | Hodorek | .............. | A61B 17/155 606/87 |
| 2011/0245927 A1 * | 10/2011 | Farris | ..................... | A61F 2/442 623/17.16 |

* cited by examiner

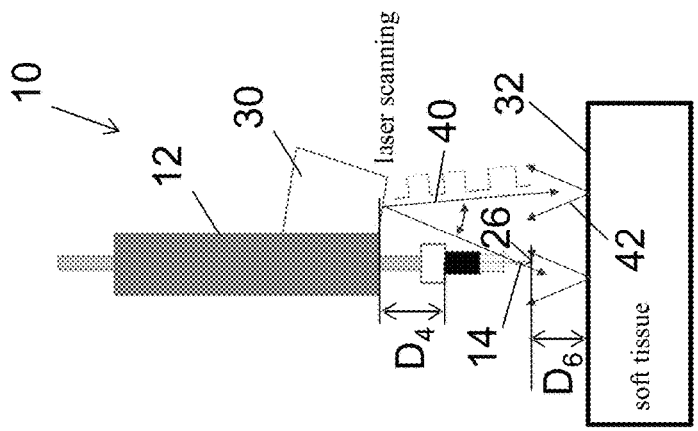
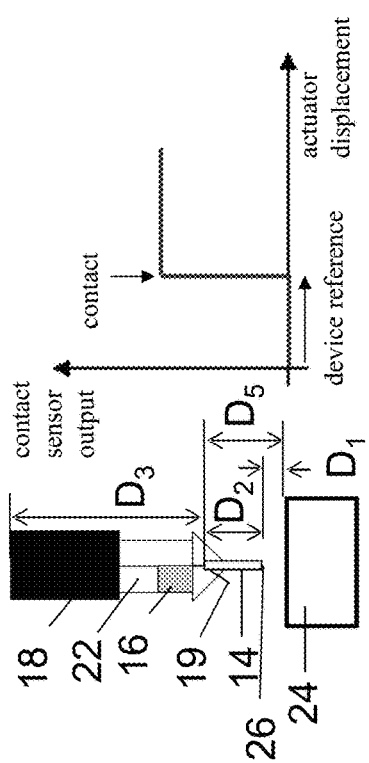
Fig. 6A
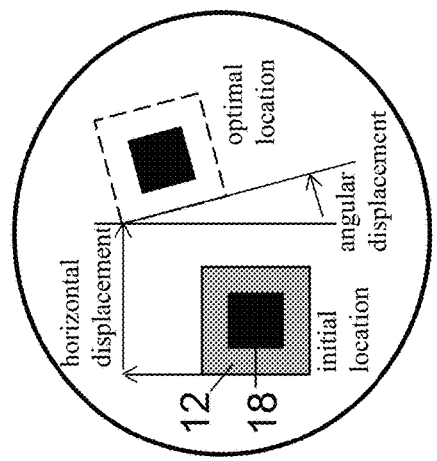
Fig. 6B
Fig. 6C

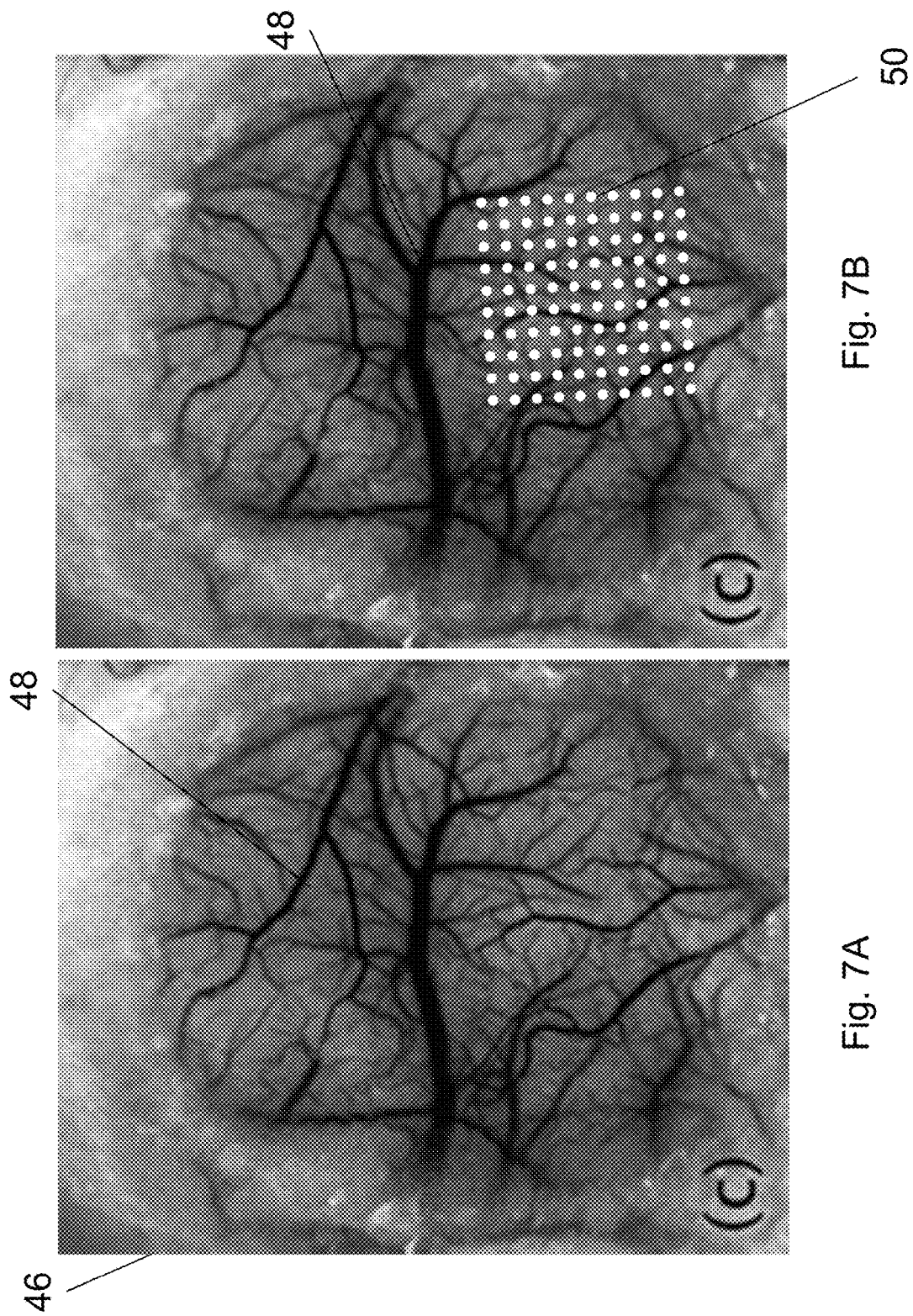

FIG. 11A

| Step | Description |
|---|---|
| Step 22 | Identify that horizontal and angular position of the implantation sites 50 that leads to the minimum overlap area between the implantation sites 50 and the tissue structures subject to damage by device implantation |
| Step 23 | Overlay the projection of the implantation sites 50 for this horizontal and angular position onto the live video image of the implantation location in green, for example |
| Step 24 | Optional - Prompt the surgeon to accept this implantation location or make a manual adjustment of the software projection of the implantation sites on the live video image |
| Step 25 | Optional - Finalize the position and orientation of the implantation sites at the implantation location |
| Step 26 | Move the actuator to the position and orientation defined in Step 14 and overlay the actual implantation sites on the live video image of the implantation location |
| Step 27 | Determine the vertical distance and angular relationship between the actuator and the surface of the tissue at the implantation location |
| Step 28 | Adjust the position and orientation of the actuator so the longitudinal axis of the actuator is normal to the tissue surface and the implantation location |
| Step 29 | Optional - Prompt the surgeon to make a final refinement of the implantation site, accept the current position and orientation or restart the mapping process at Step 6 |
| Step 30 | Optional - Finalize the implantation location and move the actuator to that position and orientation if a manual refinement occurred |

Fig. 11B

APPARATUS AND METHOD FOR IMPLANTATION OF DEVICES INTO SOFT TISSUE

CROSS-REFERENCE TO RELATED APPLICATIONS

The present invention is a Continuation Application of U.S. Non-provisional application Ser. No. 13/920,753, titled APPARATUS AND METHOD FOR IMPLANTATION OF DEVICES INTO SOFT TISSUE filed on Jun. 18, 2013 which claims the benefit of U.S. Provisional Application Ser. No. 61/690,044 filed Jun. 18, 2012, which is incorporated by reference herein.

STATEMENT REGARDING FEDERALLY-SPONSORED RESEARCH AND DEVELOPMENT

This invention was made with partial government support under DARPA grant N660011114025. The government has certain rights in this invention.

FIELD OF THE INVENTION

The invention relates to apparatus and methods for the surgical implantation into soft tissue of devices, such as (1) prosthetic neural interfaces between computers and the machinery they control and biological tissue, for example neurons and the nodes of Ranvier on axons in nerve bundles, (2) optical fibers for the localized stimulation of neurons and other cell types, and (3) drug delivery catheters, among others. The micrometer-scale interfaces being surgically implanted can be used for recording from the soft tissue in which they are embedded or stimulating the soft tissue in which they are embedded. The invention relates to the accurate and minimally invasive placement of prosthetic micron-scale implants at a predetermined depth, location and orientation based on the profile of the tissue, for example the vasculature of the brain, and the use of implantation-specific data like soft tissue compression force prior to penetration and frictional force between the micrometer-scale implant and the tissue after penetration to optimize final placement of the interface. The invention relates to the use of ultrasonic oscillatory motions superimposed on the main trajectory to tailor the trajectory of the implantation to realize the reduction in insertion forces and soft tissue compression, which prevents effective insertion and increases tissue damage. The invention relates to the use of multi-unit cartridges for the implantation of multiple micrometer-scale interfaces during a single surgery without retooling, to reduce surgery time and minimize the handling of the prosthetic interfaces. The invention also relates to precise control of insertion speed, and tools for visual and sensor-based inspection of insertion characteristics such as initial tissue contact and forces during insertion.

BACKGROUND OF THE INVENTION

Many implantable devices that interact with tissue, including those used in surgical procedures, in-vitro tests, and in-vivo implantations, require special care for accurate positioning (location and orientation) of the implantation device. Furthermore, a critical issue is to ensure that implantation occurs satisfactorily; that is, the device is inserted in at the required depth without device failure. Manual insertions of devices cannot provide this level of control in positioning and insertion, therefore leading to high rate of device failure during insertion, over-design of devices with larger-than-needed foreign materials, and functional failures. An important need is to have automated mechanisms for insertion, that provide precision in positioning (cellular-scale, approximately 20 µm), orientation (±0.5°), and speed control (±1%), as well as allow feedback and evaluation through visual and sensor-based in-situ characterization capability.

An illustrative example of this need arises from the insertion of the neural probes for brain-computer interfaces (BCI). Research on BCI and brain-machine interfaces (BMI) in recent years has demonstrated the feasibility of driving motor prostheses for the upper limbs of amputees and for restoring mobility to quadriplegics and tetraplegics whose condition arose due to injury or disease. More recently, research has begun to focus on providing feedback loops between the brain and other nervous tissue and the computers and machines to which they are interfaced by stimulating the tissue with signals from the external equipment to return sensation to BMI and BCI recipients. In this way, an injured or diseased individual can control an external prosthetic and receive sensation from it in a way that naturalistically mimics the limb they lost or the biological function that is impaired.

BCIs and BMIs comprise: 1. an interface to the soft tissue that records the electrical, chemical or mechanical activity of the soft tissue and transduces it to a signal in a suitable energy domain, typically electrical, 2. a decoder that extracts the information from the signals received from the tissue, 3. a transmitter that sends out the decoded signals, 4. a receiver of the decoded signal, 5. a computer or machine that acts under the instructions carried in the decoded signals, 6. a sensor array that detects changes in the environment caused by the action of the computer or the machine and transduces it to a signal in a suitable energy domain, 7. an encoder that receives the output of the sensor array and converts it to a sensory signal for transmission, 8. a transmitter that sends out the encoded sensory signals, 9. a receiver of the encoded sensory signals, and 10. an interface that transduces the encoded sensory signals to an electrical, chemical or mechanical signal for stimulation of the soft tissue in which the interface is embedded.

The interface is a critical feature of BMIs and BCIs and its placement must be as close as possible to the biological signal sources without damaging them in order to maximize the information extracted from the soft tissue and minimize the amount of energy needed to transmit sensory information back into the soft tissue. The most common interface is the electrode. Typically, this is an insulated, electrically conductive material with a small surface exposed to the soft tissue environment. Electrodes have dimensions ranging from 10 s of micrometers to 100 s of micrometers. The effectiveness, stability and reliability of these interfaces has been identified in the literature, in part, as dependent on the method of implantation and the accuracy of their placement. Interface reliability is a critical research area where progress is needed prior to transitioning BMI and BCI technology for practical restoration of motor and sensory functions in humans. Two key issues are 1) the inability of current interfaces to reliably obtain accurate information from tissue over a period of decades, and 2) currently measured signals from tissue cannot be reliably used to control high degree-of-freedom (DOF) prostheses with high speed and resolution.

Failure of biological soft tissue interfaces may be caused by several issues. After implantation, current probes are surrounded by reactive microglia and reactive astrocyte scarring as shown pictorially in FIG. 1(a). In the brain, damage to the neural vasculature causes a breach in the blood-brain barrier (BBB) that is associated with reactive soft tissue responses. Tissue reaction with the probe results in encapsulation that insulates the electrode by impeding diffusion of chemical and ionic species and may impede current flow from the soft tissue to the interfaces. Encapsulation increases the distance of the electrode from active neurons. For viable recording, the distance of the electrode from active neurons must be less than 100 μm. Progressive death and degeneration of neurons in the zone around the inserted probe due to chronic inflammation may eliminate neural electrophysiological activity. Lastly, interconnects may fatigue and break due to stresses. Experiments in animals have resulted in some neural electrode sites failing while others keep working for several years. This variability in outcome is believed to be due to several factors including variable BBB damage, variable scar formation, mechanical strain from micromotion, inflammation, microglial condition and disconnected neurons.

Tissue interfaces employed today for BMI and BCI applications come in a variety of shapes made of many materials and apparatus and methods for implanting these interfaces must have the functional and design flexibility to handle the multiplicity of devices available today and accommodate the designs and forms that become dominant as the technology matures and moves into widespread human use. In the next few paragraphs, the challenge presented by the range of device types and materials will be established by reviewing the devices described in the literature.

Historically, the interfaces have been stiff needles usually made from wires, silicon or glass. Metal wire neural probes are typically 50-100 μm in diameter and usually made of platinum or iridium and insulated with glass, Teflon, polyimide or parylene.

Silicon-mounted interfaces made with MEMS fabrication were first introduced by Ken Wise and Jim Angell at Stanford in 1969. Ken Wise's group at the University of Michigan subsequently developed a series of silicon probes and probe arrays with multi-site electrodes.

A 2D probe array was developed at the University of Utah in 1991, known as the Utah Electrode Array (UEA). The UEA has become a favored interface in human applications in the central nervous system (CNS) and for research in the peripheral nervous system (PNS).

Polycrystalline diamond (poly-C) probes with 3 μm thick undoped poly-C on a ~1 μm $SiO_2$ layer have been fabricated by Dr. Aslam's group at Michigan State University.

Research groups have created more compliant probes made with thin-film wiring embedded in polymer insulating films. Flexible CNS probes have been made in polyimide, SU8/parylene and all parylene. These probes are still extremely stiff in both axial and transverse directions relative to brain tissue, which has a Young's modulus of approximately 30 kPa. Any axial force transmitted through the external cabling directly acts on the probe and creates shear forces at the electrode-tissue interfaces. Such forces may come from external motion or from tissue growth around the implant. To address this issue, a group from Carnegie Mellon University and the University of Pittsburgh have developed a parylene-coated Pt probe with a thickness of 2.5 μm and width 10 μm that provides axial strain relief in the brain through a meandered design (FIG. 1(b)). The cables external to the brain are also meandered to further reduce transmission of brain-skull relative motion to the embedded probe. Because of the size and compliance of the meandered probes they are embedded in a biodissolvable delivery vehicle which provides the stiff structure for implantation.

A team from Drexel Univ., the Univ. of Kentucky and SUNY created ceramic-based multisite microelectrode arrays on alumina substrates with thickness ranging from 38 to 50 μm, platinum recording sites of 22 μm×80 μm, and insulation using 0.1 μm ion-beam assisted deposition of alumina.

Y.-C. Tai's group at Caltech produced parylene-coated silicon probes with integral parylene cabling, shown in FIG. 2(a). The shanks were up to 12 mm long. A primary innovation was a flexible 10 μm-thick, 830 μm-wide, 2.5 mm-long parylene cable.

Flexible polyimide probe arrays (FIG. 2(c)) have been made with gold electrodes. These probes must be inserted by first creating an insertion hole with a scalpel or needle. A later polyimide probe array incorporated silicon for selected locations along the length of the shank, with polyimide connectors to create enhanced compliance, as shown in FIG. 2(b).

An innovative all-polymer probe design incorporated a lateral lattice-like parylene structure attached to a larger SU8 shank to reduce the structural size close to the electrodes. The lattice structure, shown in FIG. 2(e), included a 4 μm-wide, 5 μm-thick lateral beam located parallel to the main shank. Encapsulating cell density around the lateral beam was reduced by one-third relative to the larger shank. While the structure was non-functional, it is presumed that placing electrode sites on the smaller beam would result in superior recording performance.

U.S. patent application 20090099441 from Dr. Giszter's Drexel group describes biodegradable stiffening wires 1 braided with electrode wires 2 (see FIG. 2(f)) where flexible wires 2 are braided onto a maypole structure 4 with stiff biodegradable strands 1. When the biodegradable strands 1 dissolve, the flexible wiring 2 is left in the brain tissue. These braided composite electrodes are similar in spirit to present invention. However, reliable and manufacturable connections to the braided wires become difficult when scaled to arrays.

Olbricht et al has reported on flexible microfluidic devices supported by biodegradable insertion scaffolds for convection-enhanced neural drug delivery. The device consists of a flexible parylene-C microfluidic channel that is supported during its insertion into tissue by a biodegradable poly(DL-lactide-co-glycolide) (PLGA) scaffold. The scaffold is made separately by hot embossing the PLGA material into a mold.

Tyler et al, have developed a neural probe made from a polymer nanocomposite of poly(vinyl acetate) (PVAc) and tunicate whiskers, inspired by the sea cucumber dermis. The probe material exhibits a real part of the elastic modulus (tensile storage modulus) of 5 GPa after fabrication. When exposed to physiological fluid conditions, its modulus decreases to 12 MPa.

The trend in devices is towards more compliant materials and structures that will have stringent implantation requirements in terms of speed, force and placement. In the following paragraphs, the state-of-the-art in soft tissue interface insertion technology is described.

Manual implantation or stereotaxic assisted implantation by a skilled surgeon is the most common method of implantation of the variety of interfaces and interface delivery vehicles described above. Manual implantation means the procedure is done by hand and stereotaxic assisted implantation means it is done through the use of a stereotaxic frame that holds the interface delivery vehicle and provides a hand operated screwdrive to position and insert the interface. Positioning is usually performed with the assistance of a stereomicroscope that provides some measure of depth perception. With this technique, there is no control over the speed of insertion and only gross sensitivity to the profile of the underlying soft tissue, both of which could contribute to the variability observed in the outcomes of soft tissue interface implantations. Insertions of the Michigan probe array are done using this method.

The low velocity of manual insertions, either by hand or using stereotaxic frames, results in observable soft tissue dimpling prior to penetration of the tissue. Dimpling was found to be accompanied by soft tissue compression that resulted in damage to the tissue and reduced signal extraction.

To improve outcomes by reducing manual variability and increasing insertion speed, research groups adopted a handheld pneumatic insertion device invented by Normann et al. and experimentally demonstrated by Rousche and Normann. The pneumatic inserter has a piston mechanism that is actuated pneumatically to strike an endpiece rod on which is adhered the device to be implanted. The burst of pressure accelerates the piston and its momentum is transferred to the endpiece rod which is driven toward the brain at speeds of 8 m/s, which was found to be required for the 10 electrode×1 electrode interface to penetrate the soft tissue. An adverse effect of the mechanism is recoil of the endpiece due to the return spring which can lead to retraction of the interface device if it remains adhered to the endpiece. Researchers using the UEA avoid this effect by resting the interface on the tissue into which it will be implanted and using the endpiece to strike the back of the interface device. This technique does not allow for accurate placement of the interface in soft tissue because there is no visibility of the contact points between the interface and the tissue. House et al. achieved a measure of control over the spatial relationship between the endpiece and the device to be inserted by mounting the pneumatic inserter on a stereotaxic manipulator. They found the impact between the endpiece and the backside of the interface often led to damage of the interface, so they added a "footplate" to the device. However, because the device is not mechanically connected to a fixed reference structure, it is subject to elastic recoil from the soft tissue into which it is implanted and this can lead to retraction of the interface from the tissue. To overcome retraction the interface must be over-driven into the soft tissue so that after recoil, the full length of the interface remains in the tissue. The literature does not have detailed studies on the impact of over-driving the insertion on the health of the recipient.

The literature reports other insertion mechanisms of varying levels of complexity and functionality. Rennaker et al. reported a manually positioned spring-driven hammer mechanism for insertions up to 1.5 m/s for microwires mounted on the insertion device using a locking screw. Jensen et al. reported a hydraulically driven micromanipulator with manual positioning and force sensing and a speed of 2 mm/s. Dimaio and Salcudean used a robotic manipulator to implant 17 gauge epidural needles with force sensing but did not report the insertion speeds they achieved. Bjornsson et al. used stepper motors to implant Si microneedles at up to 2 mm/s with force sensing. Sharp et al. electronically controlled a micromanipulator with an in-line load cell to achieve insertion speeds from 11 µm/s to 822 µm/s for evaluation of penetration mechanics in cerebral cortex. In each of these cases and others in the literature, fine positioning, if done, was performed by visually locating the interface over the soft tissue to be implanted.

Accurate placement of the interface requires referencing of the tissue height, maintaining the relative height between the interface mounted on the insertion apparatus and the tissue as the tissue surface moves under pulsatile and respiratory motion, mapping and identifying the insertion location with an overlay of the interfaces and positioning the interface in space with respect to the tissue surface. This is an area where the literature is very sparse. Kozai et at used two photon imaging to map the cortical vasculature to identify target locations prior to interface implantation and found that when this is done the trauma of implantation can be reduced by 73% for surface vasculature compared to the case when vasculature is targeted.

SUMMARY OF THE INVENTION

The present invention describes an apparatus and method for implanting devices into soft tissue with accuracy and precision in three dimensions as well as in prescribed insertion speed and trajectory, and reduces the damage that occurs to the soft tissue into which the device is implanted.

The invention apparatus comprises several sub-systems that provide the functionality to achieve accuracy, precision and damage reduction. These subsystems are: 1. an actuator, such as the M272 piezo motor sold by PI of Auburn, Mass., that moves at a controlled high velocity along a single, longitudinal axis (i.e the implantation trajectory) with a large travel range up to 50 mm and better than 20 micron positional accuracy; 2. an actuator, such as that made from K-740 PZT by Piezo Technologies, Indianapolis, Ind. that can impart an oscillatory motion at frequencies between 18 kHz and 30 kHz in two directions, corresponding to the transverse directions to the insertion direction, or the single, longitudinal axis) for reduction of insertion forces; 3. a load cell, such as the Sensotec Model 31 sold by Honeywell of Morristown, N.J., that measures the force between the device being implanted and the tissue surface during implantation; 4. a contact sensor for accurate detection of the point and time of contact between the soft tissue and the device being implanted, which can be achieved by monitoring the electrical characteristics of the piezo-actuator described in subsystem 2; 5. a laser ranging system, like the Hokuyo URG-04LX-UG01 with a Sokuiki sensor, for referencing the position and motion of the tissue with respect to the insertion system and the device being implanted; 6. an imaging system, such as the SE-1008-400× video microscope from Selectech Electronics of Guangdong, China, for identifying the optimal insertion location to minimize mechanical damage to tissue vasculature; 7. a clamping mechanism, such as an MGP800 series clamp from Sommer Automatic of Ettlingen, Germany, to hold the device being implanted, that is operated in coordination with the actuator; 8. a set of clamping surfaces with a design that is customized to the form of the device being implanted; 9. a cartridge for holding multiple devices with a design that is customized to the form of the device being implanted; 10. a dispenser that moves devices from the cartridge to the clamp, with a design that is customized to the form of the device being implanted, or an operating sequence in which the cartridge is stationary and the actuator and clamp execute a predefined sequence to move to the next device to be implanted and pick it up in the clamp; and 11. the action of the system and its various subsystems are coordinated using software such as Labview from National Instruments of Austin, Tex. which can provide a graphical user interface for ease of use, data acquisition from the various subsystems for real-time monitoring of the insertion procedure and offline analysis for diagnostic and clinical evaluation. A software like Matlab's Image Processing module from Mathworks of Natick, Mass., can provide the capability of capturing and manipulating image data and processing them according to a variety of algorithms that identify sensitive tissue structures, overlay images of the implantation sites and compute overlap area of sensitive tissue structures and implantation sites.

The method of the invention in summary is: 1. device loading; 2. device referencing; 3. implantation location identification; 4 optional surgeon final adjustment; 5. tissue height referencing; 6. implantation; 7. device release; and 8. actuator retraction.

BRIEF DESCRIPTION OF THE DRAWINGS

FIGS. 6A, 6B and 6C show schematic drawings of the referencing procedure for device and tissue surface and the translation and rotation of the actuator from its initial location to its optimal location;

FIGS. 7A and 7B show an image of the surface of the field of view of an implantation location in the brain and a virtual representation of the implantation sites overlaid on the surface of the brain.

FIGS. 11A and 11B is a process flow diagram of an exemplary process of the present invention in which the optimal implantation location for the device being implanted is identified;

DETAILED DESCRIPTION OF THE INVENTION

Figure 13:
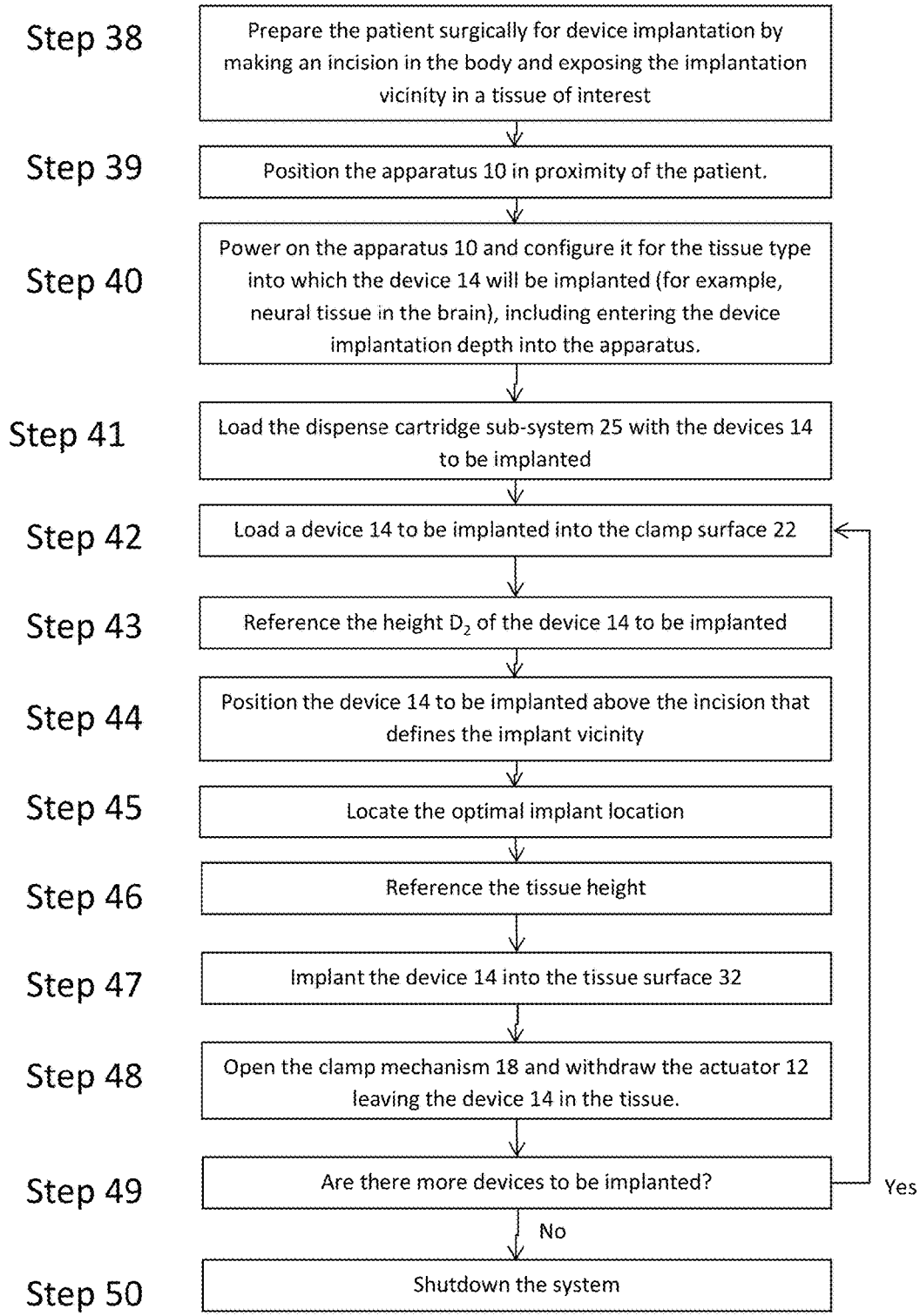
FIG. 13 is a process flow diagram of and exemplary process of the present invention in which the system is operated at a high level

The present invention addresses the problem of the accurate and precise placement and depth of devices implanted into human tissue with reduced soft tissue damage. Now turning to FIGS. 5 and 14, the present invention is an apparatus 10 for holding, referencing, targeting, and implanting devices of various sizes, shapes and materials into soft tissue and the method that must be followed for the achievement of accuracy, precision and reduced damage using the apparatus. The apparatus 10, by way of representation and not invention limitation, can include an actuator 12, laser ranging sub-system 30, contact sensor 16, load cell 20, imaging sub-system 28, clamp mechanism 18 with clamp surface 22, processor 40, memory 42, and display 44 for implantation of device 14 into tissue surface 32 (FIG. 6B) of a patient. The high level operation of the apparatus and the method for executing implantations is detailed in the process flow diagram in FIG. 13. The step numbers are labels and are not necessarily in ordered sequence in relation to other figures, unless there is an express indication that two or more figures are related (for example, FIGS. 11A and 11B).

Step 38: Prepare the patient surgically for device implantation by making an incision in the body and exposing the implantation vicinity in a tissue of interest.

Step 39: Position the apparatus 10 in proximity of the patient.

Step 40: Power on the apparatus 10 and configure it for the tissue type into which the device 14 will be implanted (for example, neural tissue in the brain), including entering the device implantation depth into the apparatus.

Figure 8:
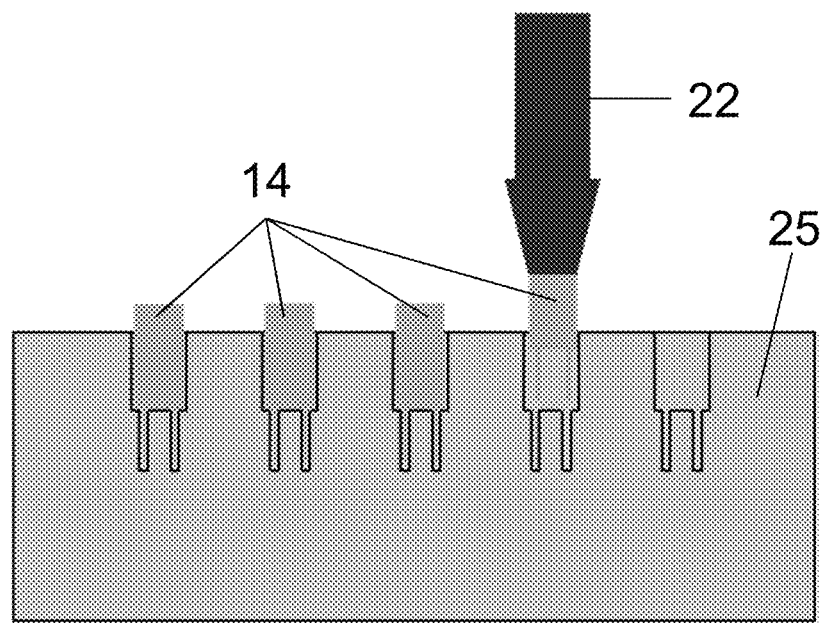
FIG. 8 shows an open section of a cartridge for holding a number of devices in preparation for implantation.

Step 41: Load the dispense cartridge sub-system 25 with the devices 14 to be implanted (FIG. 8).

Step 42: Load a device 14 to be implanted into the clamp surface 22 (FIG. 8).

Step 43: Reference the height $D_2$ of the device 14 to be implanted (FIG. 6A).

Step 44: Position the device 14 to be implanted above the incision that defines the implant vicinity (FIG. 6B).

Step 45: Locate the optimal implant location (FIG. 7).

Step 46: Reference the tissue height (FIG. 6B).

Step 47: Implant the device 14 into the tissue surface 32.

Step 48: Open the clamp mechanism 18 and withdraw the actuator 12 leaving the device 14 in the tissue.

Step 49: Are there more devices to be implanted? If yes, then go to back Step 42 repeat steps 42 to 49 until all devices are implanted. If no, then continue to Step 50.

Step 50: Shutdown the apparatus 10.

Figure 1A:
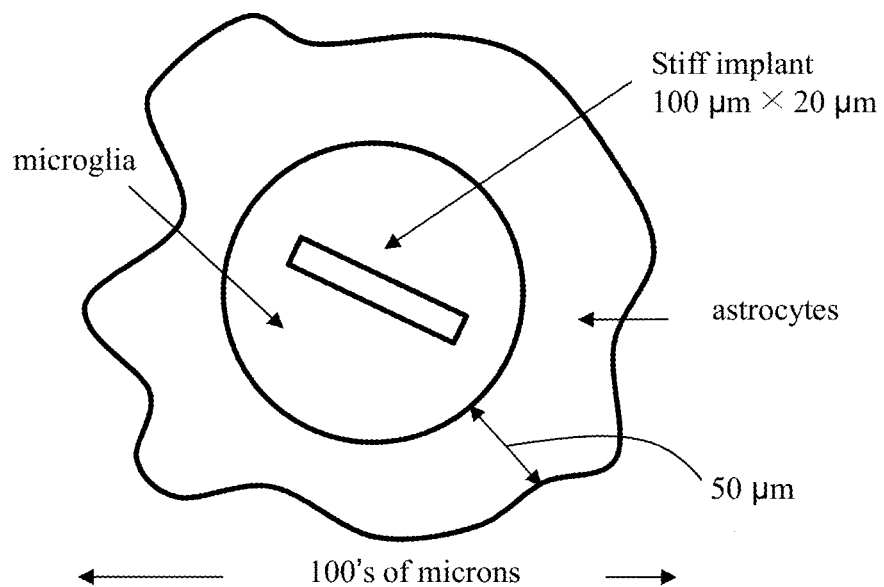
FIGS. 1A and 1B show schematics of soft tissue reactions to an implantable device in neural tissue based on its dimensions.
Figure 1B:
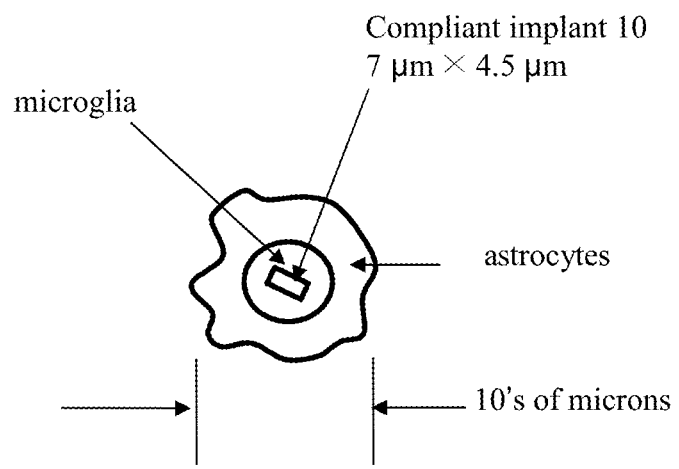
Figure 2A:
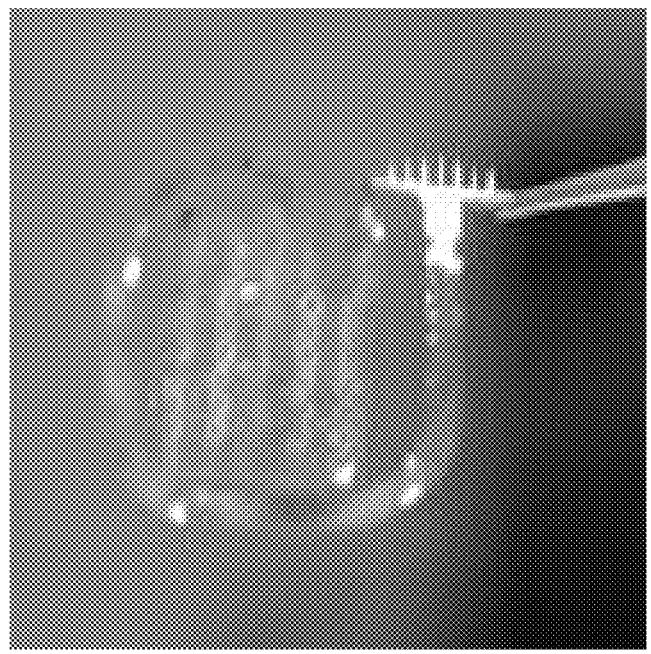
FIGS. 2a-f show a variety of implantable devices to illustrate the range of shapes and sizes the implantation apparatus must be capable of handling.
Figure 2B:
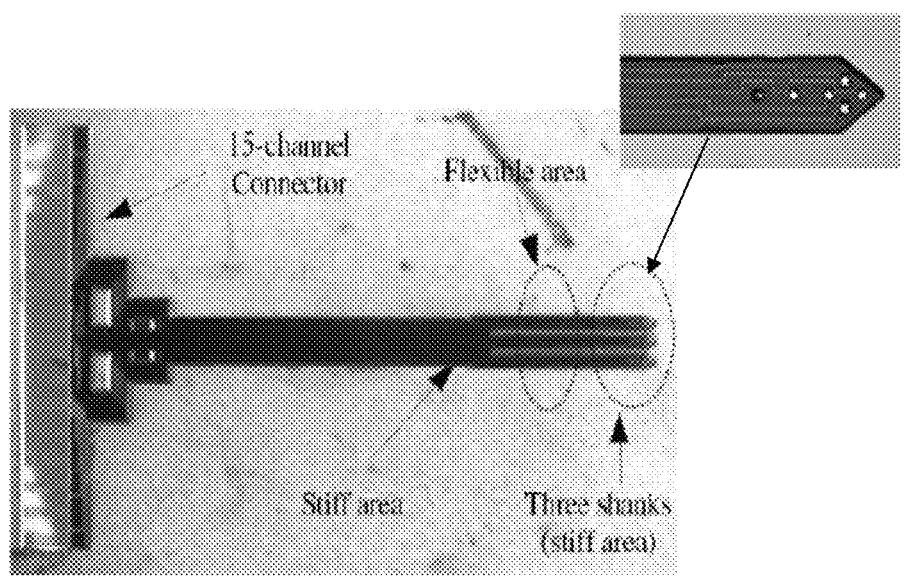
Figure 2C:
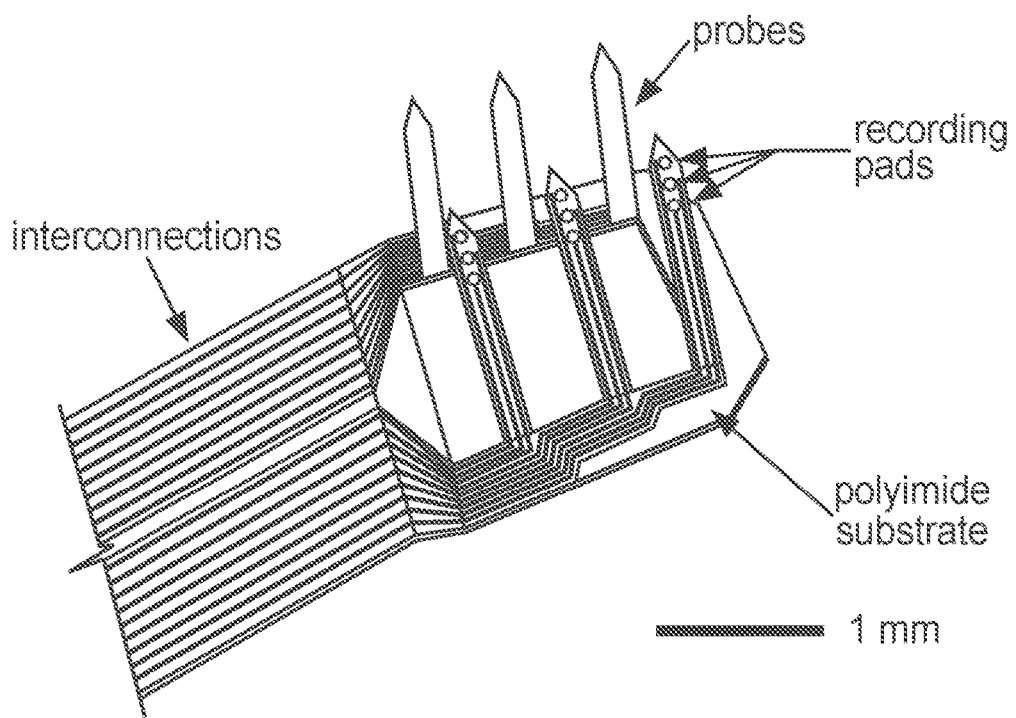
Figure 2D:
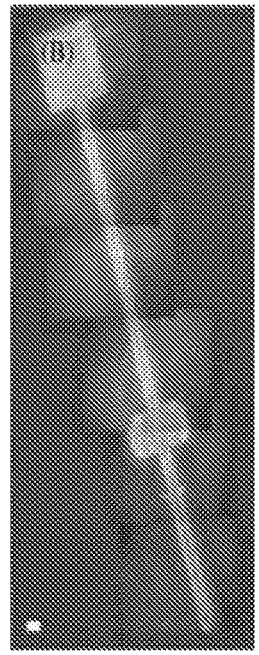
Figure 2E:
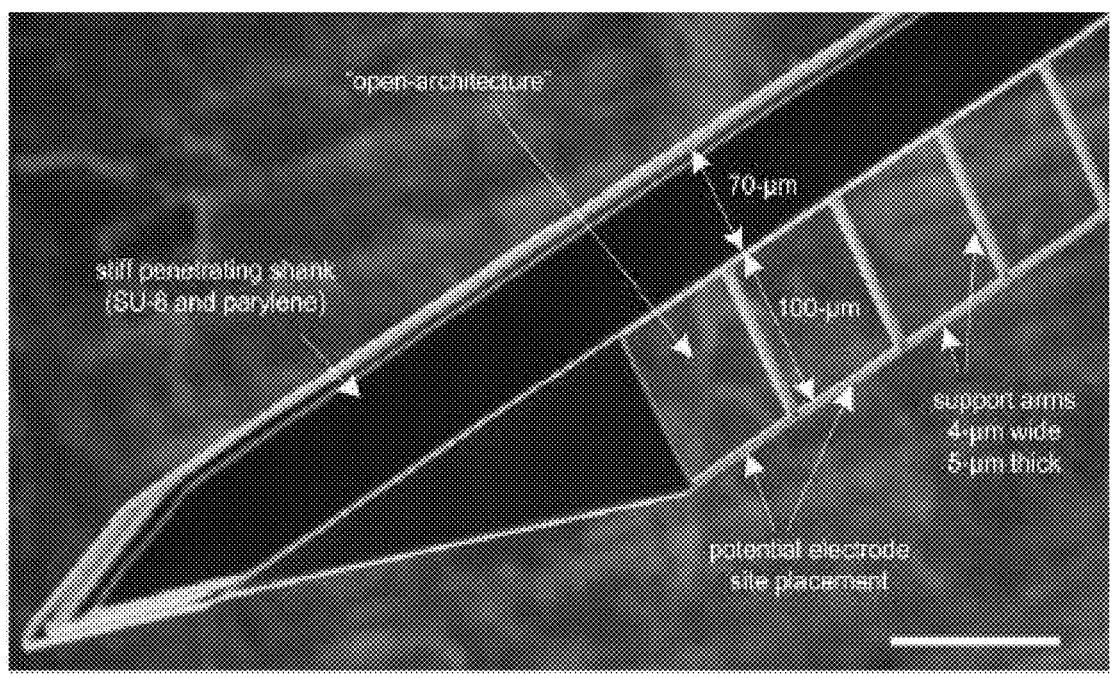
Figure 2F:
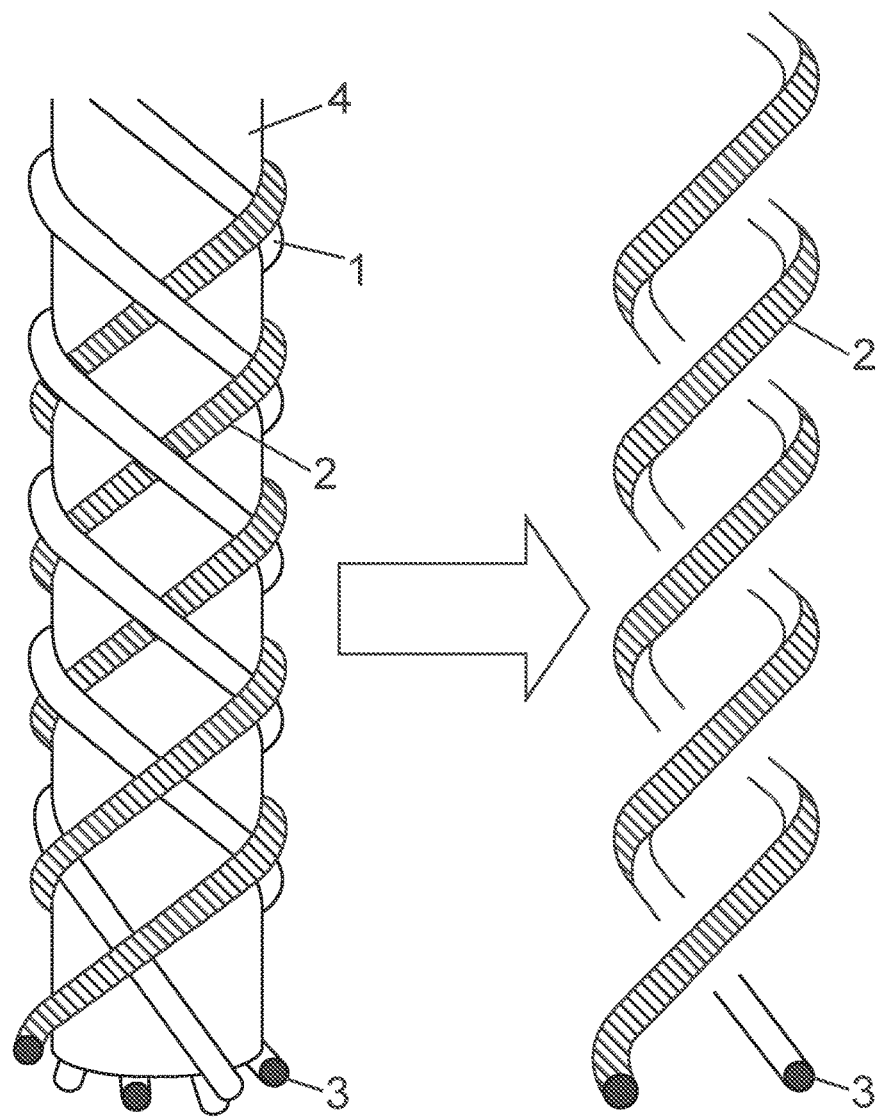
Figure 3:
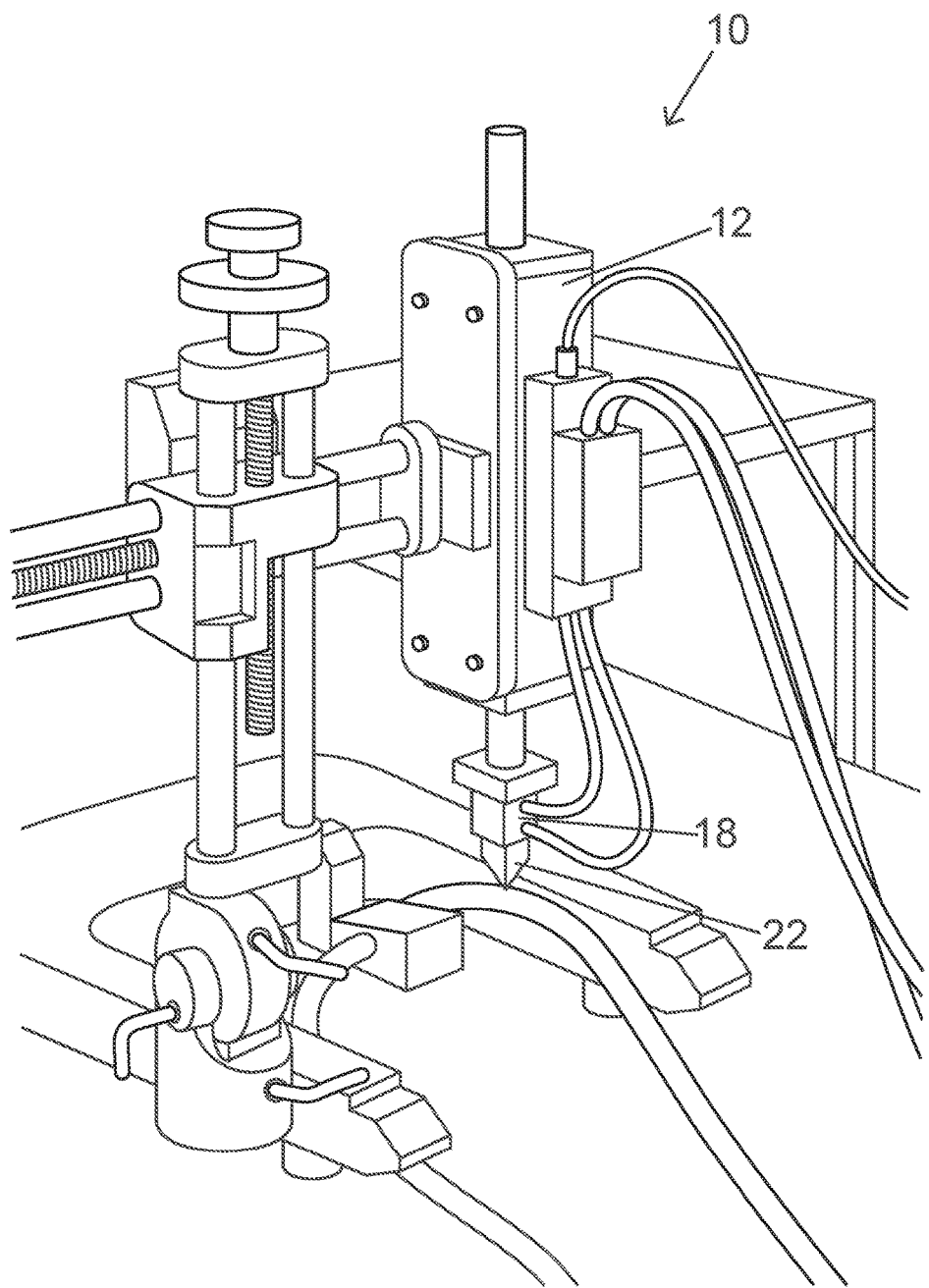
FIG. 3 shows one embodiment of an apparatus for the implantation of devices into soft tissue.
Figure 5:
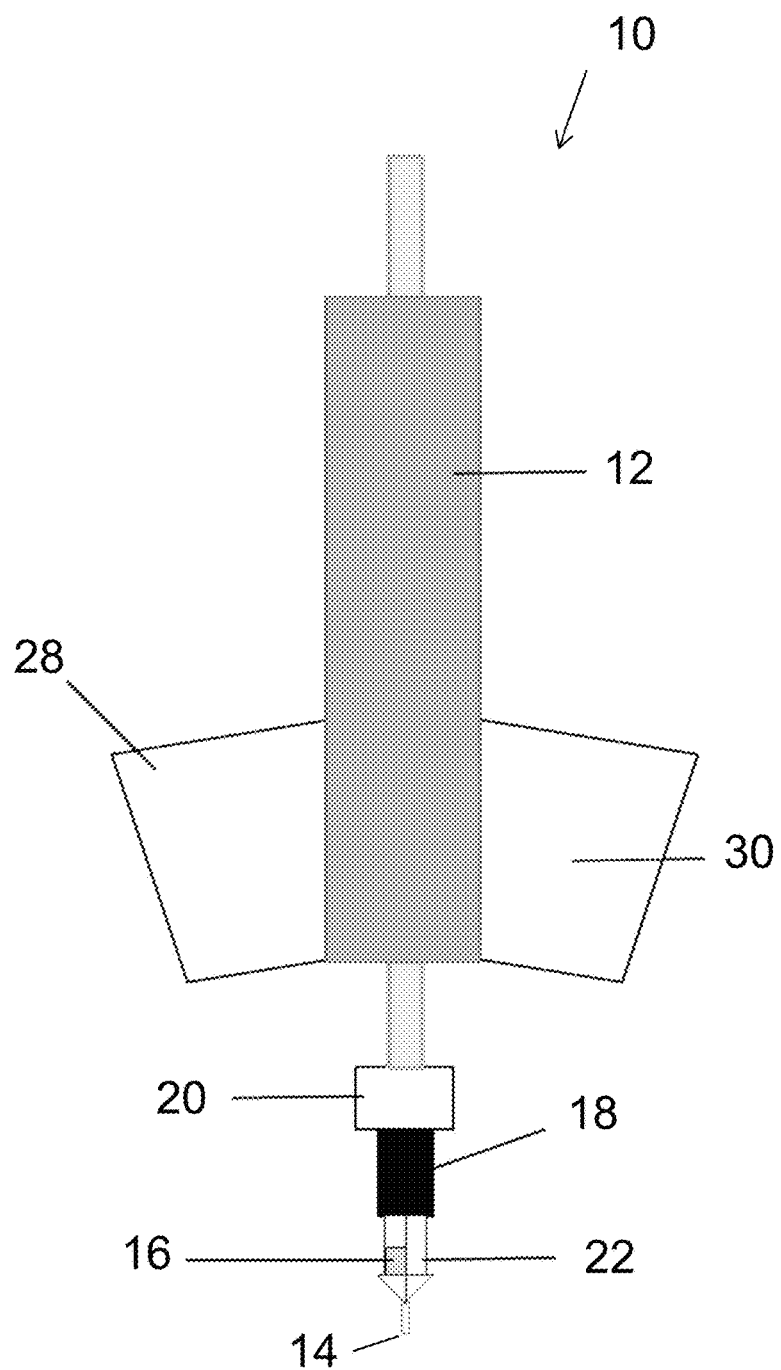
FIG. 5 shows schematic drawings of an embodiment of the apparatus with all sub-systems shown.
Figure 14:
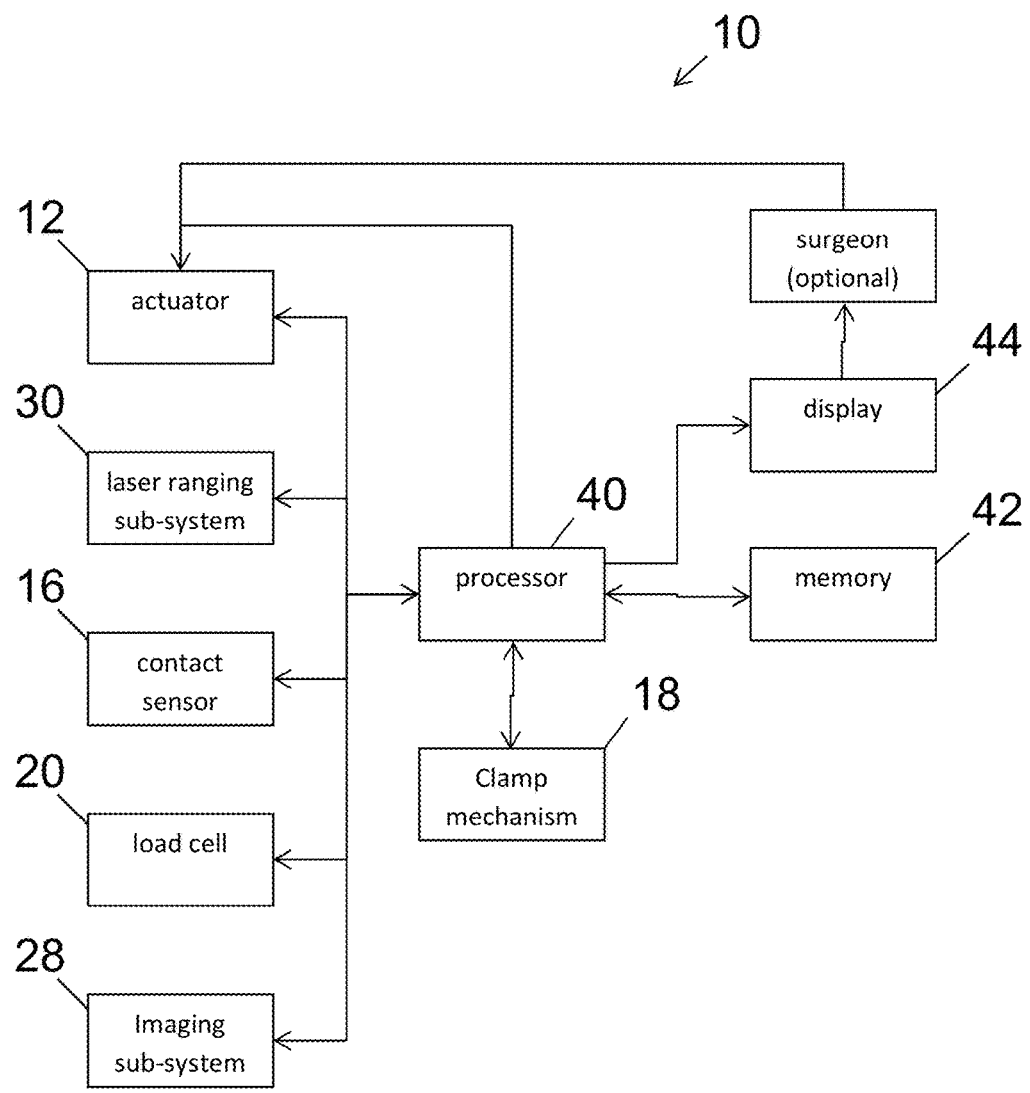
FIG. 14 is a block diagram illustrating the interconnection and functional relationships between the components and sub-systems of the apparatus

Now turning to FIGS. 3, 5, and 14, the apparatus 10 of the present invention comprises a number of sub-systems that serve particular purposes in the successful achievement of accuracy, precision and reduced soft tissue damage. Each subsystem, the function it performs and its role in the implantation method is described in detail in the following paragraphs.

Figures 4A, 4B:
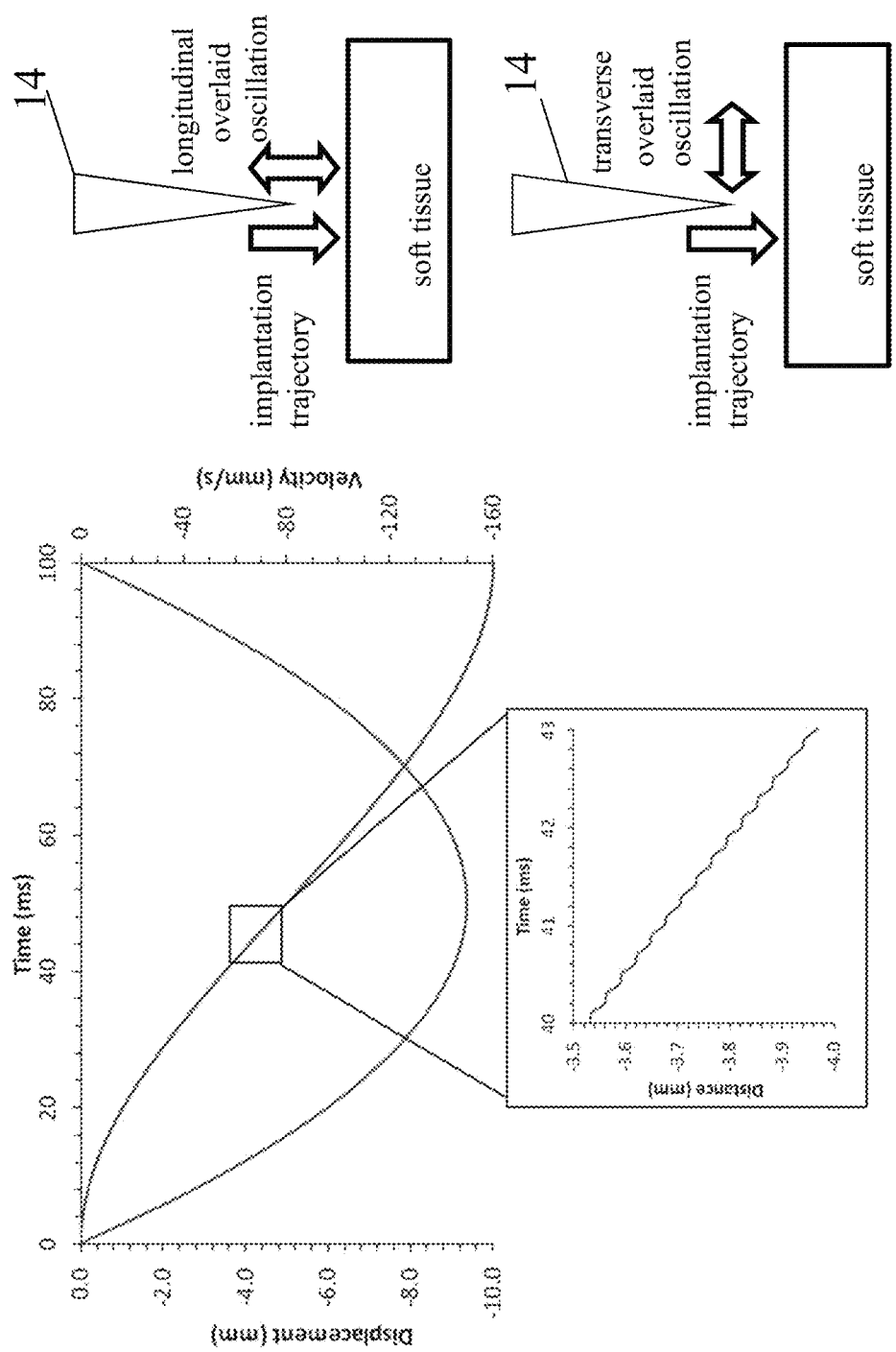
FIGS. 4A and 4B show the displacement vs. time trajectory of the device during implantation with a small amplitude ultrasonic oscillation in various planes overlaid on it.

The implantation is achieved with an actuator 12 that moves at a controlled high velocity along a single, longitudinal axis with a variable travel range (for example, several centimeters), and high precision and accuracy in the insertion trajectory (both displacement and velocity). For example, if the device 14 is to be implanted in neural tissue, which has the most stringent placement requirements, a placement accuracy of <50 microns is necessary to ensure the correct cortical neuronal layer has been implanted. The implantation orientation is also critical and should be normal to the surface being implanted to ensure no torque is applied to the device as it is implanted. In one embodiment, an orientation accuracy of ±1° to normal is preferred in the case of micron-scale, needle-shaped devices. In one embodiment of the invention (See FIG. 3), the actuator 12 is a piezomotor (like the PI M272 with a maximum velocity of 200 mm/s and a force output of 8 N) but it can be substituted with a screw-drive, a stepper motor, or another actuator (linear and/or rotational) depending on the force and velocity conditions required by the device implantation. Attached to the actuator 12 is a load cell 20 for sensing the force on the device 14 being implanted during the implantation procedure, a contact sensor 16 for detecting contact between the device 14 being implanted and the referencing tab 24 (FIG. 6A) or the tissue surface 32 (FIG. 6B), and contact been the clamping mechanism 18, that holds the device 14, and the referencing tab 24 (FIG. 6A) or the tissue surface 32 (FIG. 6B), during the referencing and implantation procedure. The dispense cartridge sub-system 25 that holds the devices 14 prior to loading into the clamping mechanism 18 is shown in FIG. 8 as a standalone component, but could be integrated into the actuator or another part of the system. The actuator 12 in some embodiments is capable of moving with a small amplitude ultrasonic oscillation overlaid on the implantation trajectory (See FIG. 4a). The force of implantation of a micron-scale device 14, like the devices that this apparatus 10 will be used to implant, can be reduced by applying ultrasonic oscillations in the range from 18 kHz to 30 kHz during implantation into soft tissue. The oscillation can be either in the direction parallel to the implantation trajectory (i.e. longitudinal), or it could be parallel to the plane of the surface of the tissue being implanted (i.e. transverse) (See FIG. 4b), Additional ultrasonic actuators can be added to achieve the oscillation, or the oscillation could be generated by modifying the drive signal of the implantation actuator to include, for example, an overlaid sinusoidal or step signal 12.

Figure 10:
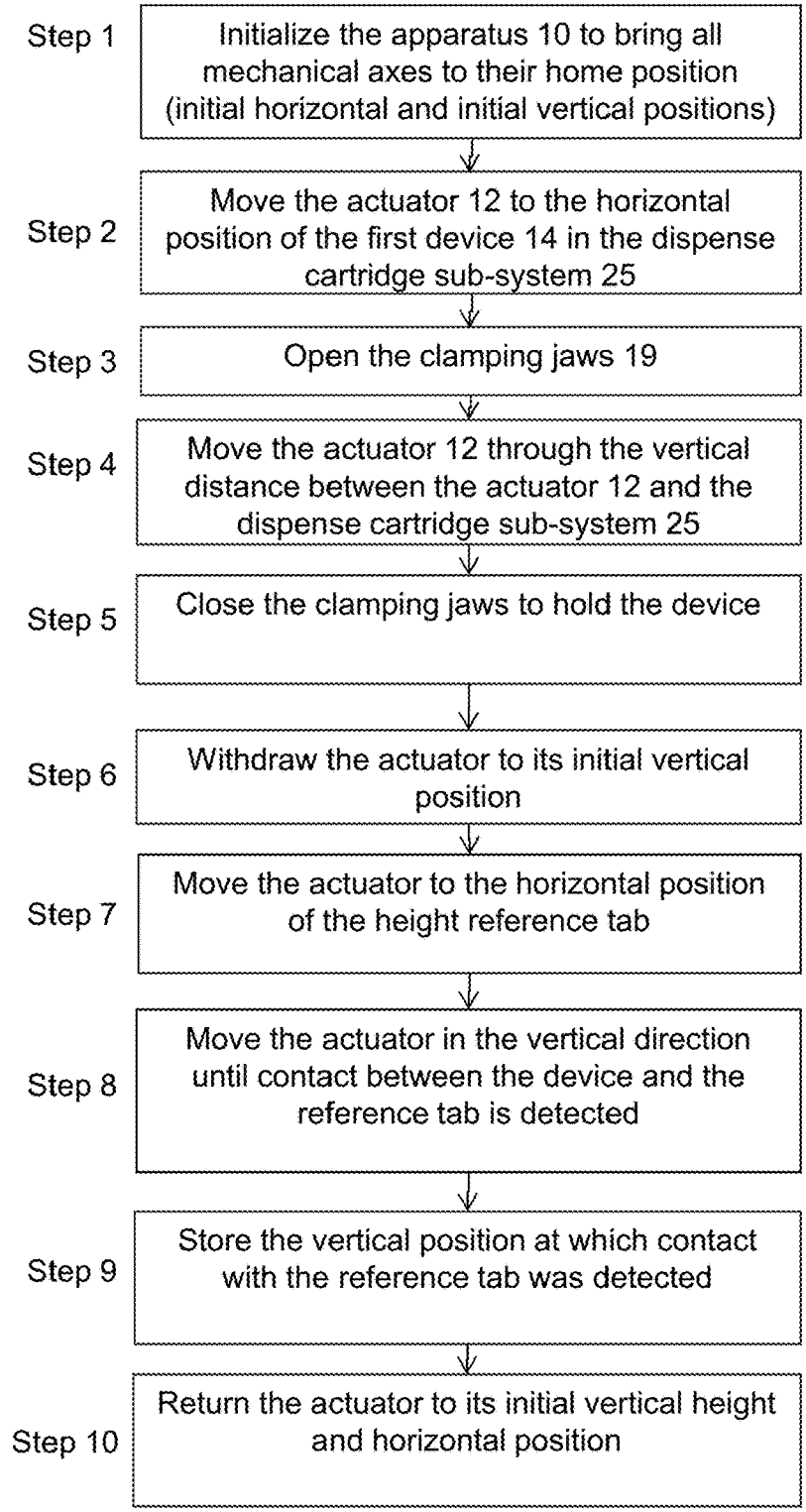
FIG. 10 is a process flow diagrams of an exemplary process of the present invention in which the device to be implanted is loaded onto an actuator and referenced for implantation into soft tissue.

Attached to the actuator 12 is a clamping mechanism 18, which can be electrically, pneumatically or magnetically driven, depending on the embodiment. In the particular embodiment shown in FIG. 3, the clamping mechanism 18 is a Techno Sommer MGP800 series pneumatic clamp. The clamping mechanism 18 has clamping jaws 22 mounted to it that is used to hold the device 14 being implanted so that it cannot change its spatial position and orientation during referencing and targeting. The process flow of loading and referencing the device 14 to be implanted is shown in FIG. 10:

Step 1: Initialize the apparatus 10 to bring all mechanical axes to their home position (initial horizontal and initial vertical positions);

Step 2: Move the actuator 12 to the horizontal position of the first device 14 in the dispense cartridge sub-system 25;

Step 3: Open the clamping jaws 19;

Step 4: Move the actuator 12 through the vertical distance between the actuator 12 and the dispense cartridge sub-system 25;

Step 5: Close the clamping jaws 19 to hold the device 14 (FIG. 8);

Step 6: Withdraw the actuator 12 to its initial vertical position;

Step 7: Move the actuator 12 to the horizontal position of the height reference tab 24 (FIG. 6A);

Step 8: Move the actuator 12 in the vertical direction until contact between the device 14 and the reference tab 24 is detected;

Step 9: Store the vertical position at which contact with the reference tab 24 was detected; and Step 10: Return the actuator 12 to its initial vertical height and horizontal position.

The various in-plane motions described in FIG. 10 and hereafter are to be understood by those versed in the art as being executed by robotic actuators with limit stops or manually through the use of locating pins.

Figure 9A:
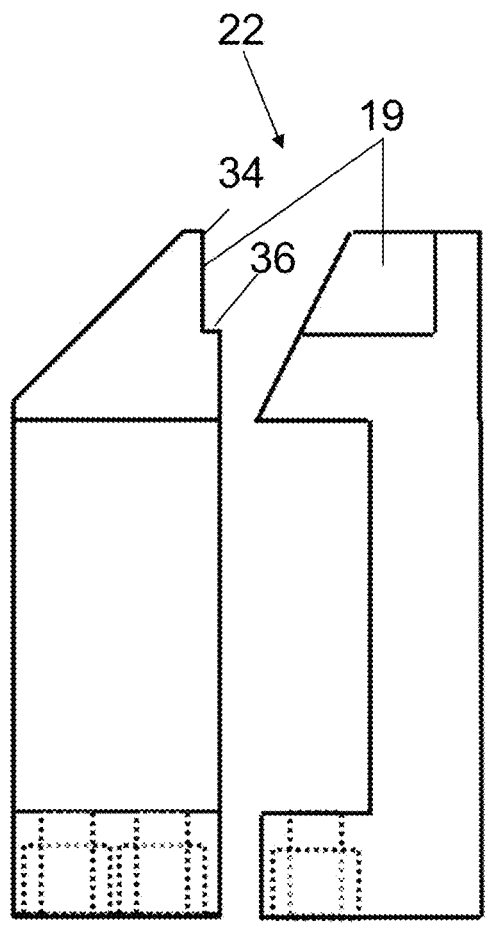
FIGS. 9 A and B show side views and face views of each side of clamping jaws used to hold the devices to be implanted.
Figure 9B:
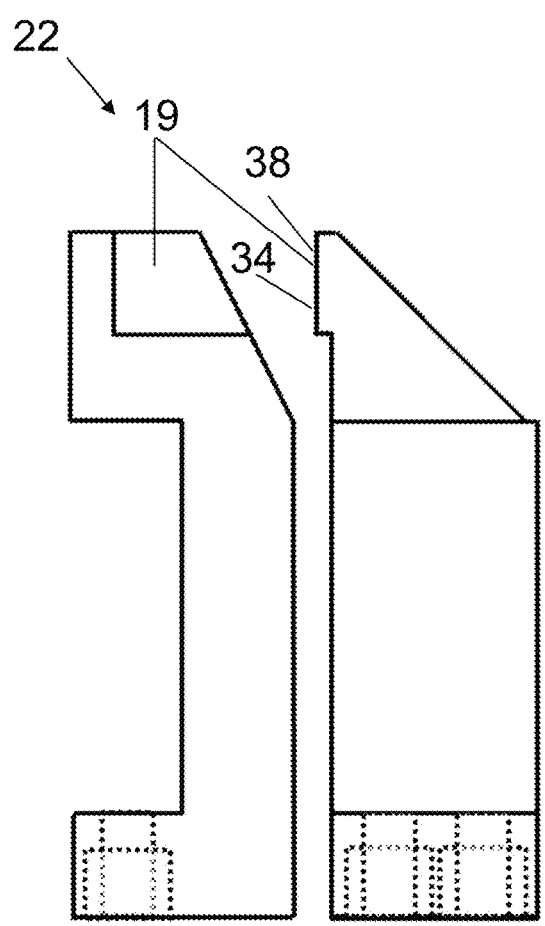

Now turning to FIGS. 9A and 9B, the clamping jaws 22 can be formed from a number of different materials, depending on the application. In the particular embodiment shown in FIG. 3, the clamping jaws 22 are made of stainless steel, but materials of varying stiffness could be used. The clamping jaws 22 have two clamping surfaces 19 on opposing faces of each jaw 22 as shown in FIG. 9a and FIG. 9b. Each clamping surface 19 has contours 34 that are designed to fix the position and orientation of the device 14 to be implanted while it is penetrating the tissue into which it is being implanted to minimize relative motion of device 14 within clamping jaw 22. On one clamping surface 19, the contour 34 is a recess 36 (FIG. 9a) and on the other face the contour 34 is a protrusion 38 (FIG. 9b), wherein protrusion 38 can be received into recess 36. Alternative embodiments of the clamping surfaces 19 can include a coating with materials that would modify their surface conditions to reduce or eliminate sticking, for example Teflon. The device 14 to be implanted can be placed manually between the clamping surfaces 19 and the clamp mechanism 18 can be closed. Alternatively, the dispense cartridge sub-system 25 shown schematically in FIG. 8 can be used to load a single device 14 and, after the device 14 has been implanted, the next device 14 will be automatically loaded from the dispense cartridge sub-system 25 into the clamping mechanism 18 until all the desired implantations are complete.

A load cell module 20, containing such load cells as the Sensotec Model 31, mounted on the actuator 12 (See schematic in FIG. 5) measures the force between the tissue and the device 14 being implanted during implantation. Knowledge of the force is a useful diagnostic for assessing soft tissue damage and implantation success and can be used during implantation as a feedback signal to control the actuator 12, either to maintain, increase or reduce the amount of force to ensure precision in depth control.

Figure 12:
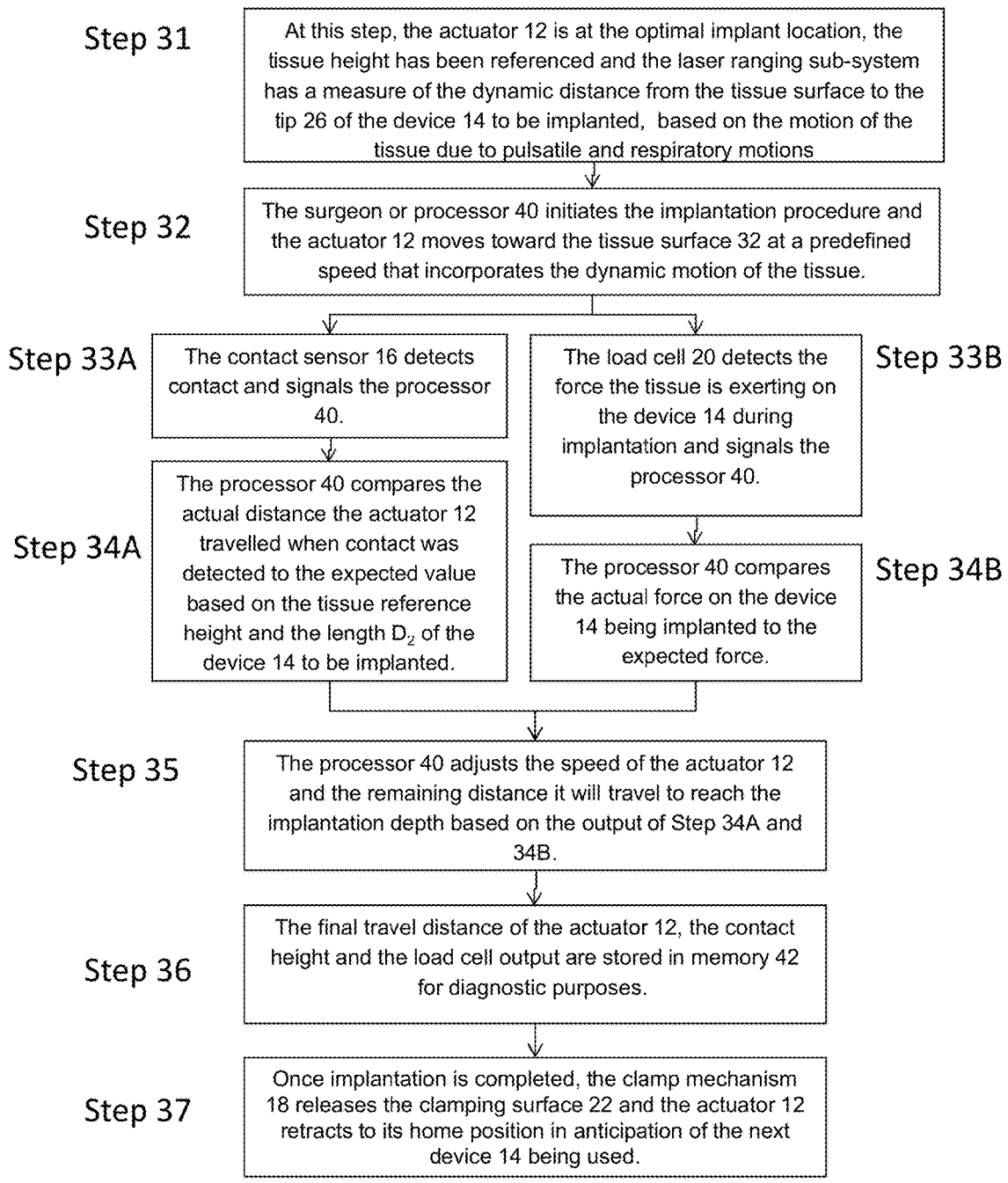
FIG. 12 is a process flow diagram of an exemplary process of the present invention in which signals from force and contact sensors are used as feedback to modify the trajectory of the actuator implanting the device into tissue.

The contact sensor 16 detects the contact of the device 14 being implanted with the tissue into which it is being implanted and the signal obtained can be used to modify the implantation conditions to ensure precision in depth control. For some devices 14, implantation must be done in a single try and their tips 26, which are extremely sharp to reduce implantation force and soft tissue dimpling during implantation would be damaged if force feedback through the load cell 20 is used to detect contact of the device 14 with a reference stage during the referencing operation so a sensor optimized for contact detection is required. Contact sensors 16, such as the ones from Kistler of Novi, Mich., have the ability to detect contact between two structures with a force of approximately 2 mN, which is below the force level that would lead to damage of the tips 26 of the device 14 being implanted. In the embodiment shown schematically in FIG. 5, the contact sensor 16 is mounted on the outer side of the clamping surfaces 19 to achieve the optimal signal to noise ratio for the contact sensor 16. After the device 14 being implanted is loaded in the clamping mechanism 18, the actuator 12 moves laterally or rotationally to a reference tab 24 and moves in the implantation direction through a distance $D_1$ until contact with the reference tab 24 is sensed (see schematic in FIG. 6A). The distance $D_1$ is measured through the software that controls the actuator 12. The position at which contact is sensed is used as a reference for the tip 26 of the device 14 being implanted to ensure the spatial relationship between the device tip 26 and the tissue surface 32 it will be implanted through is known to the positional accuracy of the actuator 12 (see FIG. 12). The distance from the laser ranging system 30 to the base of the clamp 18 is fixed by design at a distance $D_4$. The distance from the base of the clamp 18 to the recess 36 (FIG. 9A) on the clamping surface 19 of the clamp jaws 22 is fixed by design at $D_3$. The distance from the recess 36 on the clamping surface 19 of the clamp jaws 22 to the reference tab 24 is fixed by design at $D_5$. When contact between the tip 26 of the device 14 and the reference tab 24 is detected after the actuator 12 has travelled a distance $D_1$, the device 14 length $D_2$ can be calculated by $D_5-D_1$. After $D_2$ has been calculated the distance from the laser ranging system 30 to the tip of device 26 is known ($D_2+D_3+D_4$).

Figure 11A:
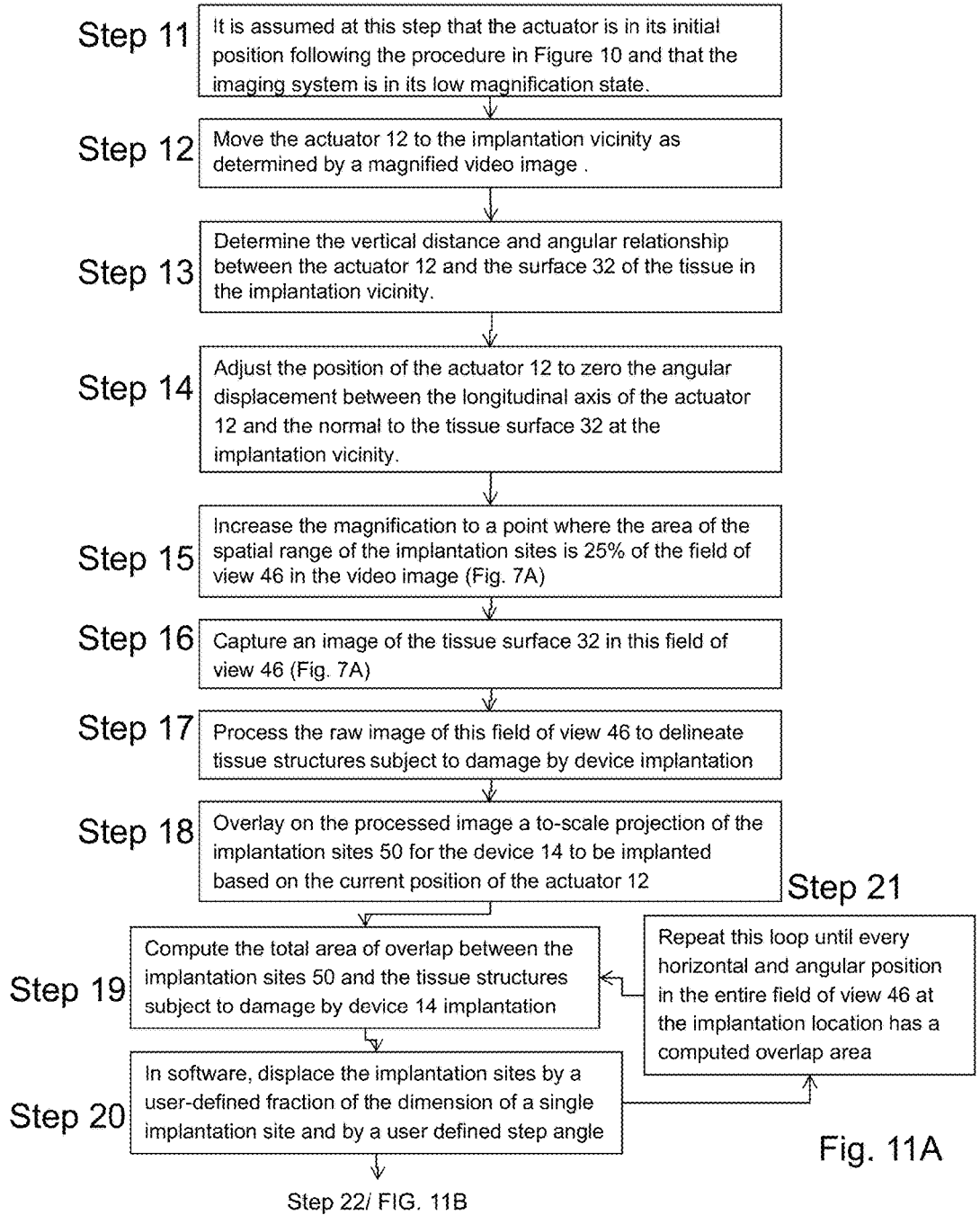

After device referencing, the surgeon performing the implantation or a processor 40 executing an automated routine uses the imaging sub-system 28 to position the device 14 being implanted above the tissue surface being implanted (see schematic in FIG. 6B), which is shown in a process flow diagram in FIGS. 11A and 11B. It is to be understood by those versed in the art that the movement of the actuator 12 during the procedure described in FIGS. 11A and 11B can be achieved using user-guided robotic control:

Step 11: It is assumed at this step that the actuator 12 is in its initial position following the procedure in FIG. 10 and that the imaging system 28 is in its low magnification state which can be on the order of 0.5× to 5×;

Step 12: Move the actuator 12 to the implantation vicinity as determined by a magnified video image;

Step 13: Determine the vertical distance and angular relationship between the actuator 12 and the surface 32 of the tissue in the implantation vicinity;

Step 14: Adjust the position of the actuator 12 to zero the angular displacement between the longitudinal axis of the actuator 12 and the normal to the tissue surface 32 at the implantation vicinity;

Step 15: Increase the magnification to a point where the area of the spatial range of the implantation sites is 25% of the field of view 46 in the video image (FIG. 7A);

Step 16: Capture an image of the tissue surface 32 in this field of view 46 (FIG. 7A);

Step 17: Process the raw image of this field of view 46 to delineate tissue structures subject to damage by device implantation, based on parameters, for example the veins 48 visible in FIGS. 7A and 7B;

Step 18: Overlay on the processed image a to-scale projection of the implantation sites 50 for the device 14 to be implanted based on the current position of the actuator 12, as shown in FIG. 7B, this is the initial implantation location;

Step 19: Compute the total area of overlap between the implantation sites 50 and the tissue structures subject to damage by device 14 implantation;

Step 20: Displace the virtual representation of the implantation sites 50 by a user-defined fraction of the dimension of a single implantation site and by a user defined step angle to a subsequent implantation location, for example, if the implantation site is 80 microns in diameter, the horizontal displacement could be 10 microns and the step angle (or angular displacement) could be 0.5° (see FIG. 6C for an illustration);

Step 21: Repeat Steps 19 and 20 until every horizontal and angular position of the implantation sites in the entire field of view 46 has a computed overlap area;

Step 22: Identify the horizontal and angular position of the implantation sites 50 that leads to the minimum overlap area between the implantation sites 50 and the tissue structures subject to damage by device implantation, this is called the optimal implantation location;

Step 23: Overlay the projection of the implantation sites 50 at the optimal implantation location onto the live video image of the field of view 46, overlay can be color coded for ease of recognition;

Step 24: Prompt the surgeon to accept this implantation location or make a manual adjustment of the software projection of the implantation sites 50 on the live video image (optional);

Step 25: Finalize the implantation location (optional);

Step 26: Move the actuator to the optimal implantation location and overlay the virtual representation of the implantation sites 50 on the live video image;

Step 27: Determine the vertical distance and angular relationship between the actuator 12 and the surface of the tissue at the implantation location using the laser ranging subsystem;

Step 28: Adjust the position and orientation of the actuator so the longitudinal axis of the actuator is normal to the tissue surface at the optimal implantation location, based on the vertical distance and angular relationship;

Step 29: Prompt the surgeon to make a final refinement of the implantation location, accept the current position and orientation or restart the mapping process at Step 16 (optional); and Step 30: Finalize the implantation location and move the actuator to that position and orientation if a manual refinement occurred (optional).

The imaging sub-system 28, such as the Selectech SE-1008-400× video microscope, has a magnification range from 0.5× to 400× that enables the identification of the implantation vicinity at low magnification and the identification of the exact implantation location at high magnification. The implantation vicinity could correspond to a hole drilled through the skull, or a vertebra, with a scale of several millimeters in diameter. The exact implantation location could be 10's of microns in diameter and a small area within the implantation vicinity. The multiple magnification scales are necessary to allow the surgeon doing the implantation to locate the small implantation location within the larger implantation vicinity. As higher magnifications also result in smaller fields of view, it is necessary to have low magnification imaging for orienting to the implantation vicinity. Through a software like Matlab's Image Processing module, a video image of the tissue surface at the implantation location, in the visual region of the electromagnetic spectrum, or the infrared region, is captured (FIG. 7a) and a virtual representation of the initial implantation site, or sites for multi-shank devices, based on the current position of the actuator 12 are overlaid on the video image of the tissue surface, as shown in FIG. 7b. The laser ranging sub-system 30 references the surface of the tissue into which the device 14 is being implanted and monitors the fine motions of the tissue due to, for example, respiratory and pulsatile motions. A laser ranging sub-system 30, such as the Hokuyo URG-04LX-UG01 Sokuiki sensor, is mounted to the body of the linear actuator 12 as shown schematically in FIG. 6B. This system works by reflecting laser beams off of the surface of the tissue, collecting the reflected light and determining variations in time taken for the light to travel from the source to the detector.

Optionally, when the surgeon is satisfied with the targeting of the device, the surgeon initiates a command to the linear actuator 12 to move with a predetermined speed to a predetermined depth from the surface 32 of the tissue based on the reference heights of the tissue surface 32 and the tip 26 of the implantation device 14. The speed and depth of the implantation must be predetermined in a separate procedure that is beyond the scope of this invention and is typically performed in either a research environment on animal models or through extensive imaging studies using technologies such as fMRI (function magnetic resonance imaging). In the embodiment shown in FIG. 3, the maximum speed is 200 m/s with a positional accuracy of 10 microns. During implantation the signals from the load cell 20 and the contact sensor 16 are used to control the trajectory of the actuator and compensate for the difference between predicted insertion forces and contact points and measured insertion forces and contact points. The algorithm for controlling the trajectory of the actuator is laid out in FIG. 12.

Step 31: At this step, the actuator 12 is at the optimal implant location, the tissue height has been referenced and the laser ranging sub-system 30 has a measure of the dynamic distance from the tissue surface 32 to the tip 26 of the device 14 to be implanted, based on the motion of the tissue surface 32 due to pulsatile and respiratory motions Step 32: The surgeon or processor 40 initiates the implantation procedure and the actuator 12 moves toward the tissue surface 32 at a predefined speed that incorporates the dynamic motion of the tissue.

Step 33A: The contact sensor 16 detects contact and signals the processor 40.

Step 33B: The load cell 20 detects the force the tissue is exerting on the device 14 during implantation and signals the processor 40.

Step 34A: The processor 40 compares the actual distance the actuator 12 travelled when contact was detected to the expected value based on the tissue reference height and the length $D_2$ of the device 14 to be implanted.

Step 34B: The processor 40 compares the actual force on the device 14 being implanted to the expected force.

Step 35: The processor 40 adjusts the speed of the actuator 12 and the remaining distance it will travel to reach the implantation depth based on the output of Step 34A and 34B.

Step 36: The final travel distance of the actuator 12, the contact height and the load cell output are stored in memory 42 for diagnostic purposes.

Step 37: Once implantation is completed, the clamp mechanism 18 releases the clamping surface 22 and the actuator 12 retracts to its home position in anticipation of the next device 14 being used.

Another embodiment of the invention monitors body function and movement (e.g., breathing, pulse, muscle twitching or spasms, etc.) of the patient and the target tissue's relative movement to the device 14 as a function of the body function and movement. The aforementioned sub-systems (laser ranging sub-system 30, imaging sub-system 28) of the apparatus 10 can be used as monitors, but any commercially available component that performs such monitoring tasks is acceptable. The processor 40 will analyze the body functions and movements to generate a dynamic system equation or equations to synchronize the actuation of the actuator 12 for placement of the device 14 into the tissue.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method of implanting a device in tissue comprising:
positioning the device within an implant vicinity;
capturing image data of the tissue in the implant vicinity;
identifying tissue structures in the image data subject to damage by implantation of the device;
simulating damage to the tissue structures by implantation for a plurality of virtual implantation sites within the implant vicinity; and
positioning the device with respect to an implant site having a minimal amount of damage.

2. The method of claim 1, further comprising:
implanting the device in the implant site having the minimal amount of damage.

3. The method of claim 1, further comprising:
determining a vertical distance and angular orientation between the device and a surface of the tissue at the implant site having the minimal amount of damage; and
adjusting a position of the device so that a longitudinal axis of the device is normal to the surface of the tissue at the implant site having the minimal amount of damage.

4. The method of claim 2, further comprising:
measuring a force between the device and the tissue during implantation.

5. The method of claim 2, wherein the device is implanted with an actuator moving along an axis aligned with a longitudinal axis of the device.

6. The method of claim 4, further comprising:
adjusting a speed in which the device is implanted based on the measured force.

7. The method of claim 4, wherein the device will be implanted to a depth in the tissue based on a reference point on a surface of the tissue corresponding to a location of the device when a feedback force is first measured.

8. The method of claim 4, further comprising:
adjusting implantation of the device based on a difference between the measured force and a predicted force of implantation.

* * * * *